(12) United States Patent
Alves et al.

(10) Patent No.: US 6,854,345 B2
(45) Date of Patent: Feb. 15, 2005

(54) ASSEMBLIES ADAPTED TO BE AFFIXED TO CONTAINERS CONTAINING FLUID AND METHODS OF AFFIXING SUCH ASSEMBLIES TO CONTAINERS

(75) Inventors: Evaristo Orellana Alves, Sertãozinho (BR); Clóvis Catananti Júnior, Sertãozinho (BR)

(73) Assignee: SMAR Research Corporation, Holbrook, NY (US)

( * ) Notice: Subject to any disclaimer, the term of this patent is extended or adjusted under 35 U.S.C. 154(b) by 0 days.

(21) Appl. No.: 10/252,660

(22) Filed: Sep. 23, 2002

(65) Prior Publication Data

US 2004/0055379 A1 Mar. 25, 2004

(51) Int. Cl.$^7$ ................................................. G01N 1/00
(52) U.S. Cl. ................................................. 73/863.85
(58) Field of Search ........................ 73/437, 439, 32 R, 73/32 A, 434, 863.85; 702/137, 138

(56) References Cited

U.S. PATENT DOCUMENTS

| | | | |
|---|---|---|---|
| 3,486,382 A | * 12/1969 | Vivares et al. ........... | 73/863.12 |
| 3,747,411 A | * 7/1973 | McDermott et al. ...... | 73/863.54 |
| 5,604,315 A | 2/1997 | Briefer et al. | |
| 5,811,690 A | 9/1998 | Hersey | |
| 5,827,963 A | 10/1998 | Selegatto et al. | |
| 5,899,962 A | 5/1999 | Louwagie et al. | |
| 5,907,110 A | * 5/1999 | Garcia et al. ............. | 73/864.74 |
| 5,945,070 A | * 8/1999 | Kath et al. .................. | 422/101 |
| 6,234,019 B1 | 5/2001 | Caldeira | |

* cited by examiner

*Primary Examiner*—Helen Kwok
(74) *Attorney, Agent, or Firm*—Dorsey & Whitney LLP (57) ABSTRACT

An assembly adapted to be affixed to a container which contains a sample fluid, and a method of affixing the assembly to the container, are provided. In particular, a contact pressure can be applied to a surface of the container, such that a particular arrangement, which has a portion situated within an opening of the container, is affixed to the container without piercing the surface of the container. For example, the container can be a tank, the particular arrangement can be a sensor arrangement, and a further arrangement can be used to affix the particular arrangement to the container. Moreover, the contact pressure preferably can be applied to an exterior surface of the container so that the further arrangement may be more accessible to a user of the assembly.

39 Claims, 6 Drawing Sheets

ASSEMBLIES ADAPTED TO BE AFFIXED TO CONTAINERS CONTAINING FLUID AND METHODS OF AFFIXING SUCH ASSEMBLIES TO CONTAINERS

FIELD OF THE INVENTION

The present invention relates generally to an assembly adapted to be affixed to a container which contain fluid, and a method for affixing such assembly to the container. In particular, the present invention is directed to an assembly in which a contact pressure is applied to a surface of the container, such that a particular arrangement is affixed to the container without piercing the surface of the container and to a method for affixing this assembly to the container.

BACKGROUND OF THE INVENTION

Conventional arrangements (e.g., conventional sensor arrangements) may be used to determine a characteristic of fluid within a container (e.g., a tank). For example, the conventional arrangements can be used to determine a temperature of the fluid, a pressure associated with the fluid, a density of the fluid, etc. An exemplary conventional arrangement as described in U.S. Pat. No. 6,234,019, the entire disclosure of which is incorporated herein by reference, may be affixed to a top portion of a tank, and can include a housing arrangement positioned within the tank. Such conventional arrangement also may include a first sensor positioned within the tank at a first fluid level of a sample fluid, in which the first sensor is adapted to detect a fluid pressure at the first fluid level, and a second sensor positioned within the tank at a second fluid level below the first fluid level, in which the second sensor is adapted to detect a fluid pressure at the second fluid level. Moreover, the conventional arrangement includes a transmitter which is adapted to communicate with the first sensor and with the second sensor, and a calculating device that is coupled to the transmitter. The transmitter is further adapted to generate signals corresponding to the density of the sample fluid, and the calculating device is adapted to calculate the density of the sample fluid based on such signals. Another similar conventional arrangement can include a first sensor arrangement and a second sensor arrangement as described in U.S. Pat. No. 5,827,963, the entire disclosure of which is incorporated herein by reference. The first sensor arrangement can be positioned above the second sensor arrangement, and each of the sensor arrangements may be affixed to a side wall of the tank, such that the housing the sensor, and the transmitter of each of the sensor arrangements are positioned outside of the tank. Moreover, the sensor of the first sensor arrangement can detect the pressure at the first fluid level via a first opening formed in the side wall of the tank, and the sensor of the second sensor arrangement can detect the pressure at the second fluid level via a second opening formed in the side wall of the tank.

As described-above, the conventional arrangement can be affixed to the tank, e.g., to the side wall of the tank or to the top portion which covers the tank. Specifically, holes or fores may be provided through the side wall or the top of the tank, and the conventional arrangement can be affixed to the side wall or the top portion of the tank using a plurality of securing elements, such as a plurality of metallic nuts and bolts, or protrude therethrough. Nevertheless, in the conventional arrangement, the nuts and one end of each of the bolts are positioned inside the tank. Moreover, such nuts and bolts are metallic, and have roughened surfaces. When the tank is used over a period of time, the roughened surfaces of the nuts and bolts may collect residue, and such residue may adversely affect the sample fluid inside the tank.

SUMMARY OF THE INVENTION

Therefore, a need has arisen to provide an assembly adapted to be affixed to a container containing fluid, and methods of affixing the assembly to the container, which overcome the above-described and other shortcomings of the related art.

One of the advantages of the present invention is that an assembly and a method for affixing the assembly to a container are provided which is adapted to be affixed to a container without piercing (e.g., without penetrating) a surface of the container, e.g., without forming holes through the container. Another advantage of the present invention is that elements of the assembly which are positioned inside the container preferably do not have sharp edges or roughened surfaces, such that residue may not collect on those elements of the assembly which are positioned inside the container. For example, the elements of the assembly which are positioned inside the container can be manufactured from a flexible material, such as rubber. Consequently, the fluid inside the container would not be adversely affected by the elements of the assembly which are positioned inside the container.

These and other advantages can be realized with an exemplary embodiment of the present invention, in which an assembly adapted to be affixed to a container (e.g., a tank) containing fluid, and a method for affixing the assembly to the container are provided such that contact pressure is applied to a surface of the container (e.g., using a first arrangement). In this manner, a second arrangement is affixed to the container without piercing the surface of the container. Specifically, the first arrangement may be positioned in the vicinity of an opening or a fore in the container, and the second arrangement (e.g., a sensor arrangement) may include a portion situated within the opening. Moreover, the first arrangement can be adapted to affix the second arrangement to the container without piercing a surface of the container by applying the contact pressure to the surface (e.g., an exterior surface) of the container.

In another exemplary embodiment of the present invention, the second arrangement can include a housing arrangement, and a portion of the housing arrangement may be positioned inside the container, or the housing arrangement can be entirely situated outside the container. The housing arrangement can contain a first sensor fluid and a second sensor fluid, such that the housing arrangement prevents the first sensor fluid and the second sensor fluid from mixing with the sample fluid. The second arrangement also can include a first sensor positioned within the container or situated outside the container at a first fluid level. The first sensor can be connected to the housing arrangement, and may be adapted to detect a fluid pressure at the first fluid level by acting on the first sensor fluid. Similarly, the second arrangement can include a second sensor positioned within the container or situated outside the container at a second fluid level which is below the first fluid level. The second sensor can be connected to the housing arrangement, and may be adapted to detect a fluid pressure at the second fluid level by acting on the second sensor fluid. The second arrangement may further include a transmitter positioned outside the container.

The transmitter can be coupled to the housing arrangement, or may be positioned inside the housing arrangement, and the transmitter is adapted to communicate with the first sensor via the first sensor fluid and with the second sensor via the second sensor fluid. The transmitter also may be adapted to generate a signal corresponding to a density of the fluid. Moreover, the second arrangement may include a calculating device coupled to the transmitter, which is adapted to calculate the density of the fluid based on the signal.

In still another exemplary embodiment of the present invention, the first arrangement can include one or more securing elements (e.g., a threaded element, such as a bolt or a screw) positioned outside of the container. Each securing element may be directly or indirectly connected to the housing arrangement, and can also be adapted to apply the contact pressure to the surface of the container without piercing the surface of the container. For example, each securing element can apply the contact pressure to the exterior surface of the container when rotated in a predetermined direction. The first arrangement also can include a contact member (e.g., a washer) positioned between a corresponding securing element and the container. As such, each securing element may apply the contact pressure to the surface of the container via the corresponding contact member. The first arrangement can further include a plate having a hole or a plurality of holes formed therethrough. The plate can be connected to the housing arrangement, and each hole may be adapted to receive a securing element.

In yet another exemplary embodiment of the present invention, each of the sealing elements may be directly or indirectly connected to the housing arrangement, and can be mechanically coupled to the first arrangement. Moreover, when a particular securing element applies the contact pressure to a first surface of the container, such sealing element moves in a direction towards a second surface of the container. For example, when the securing element applies the contact pressure to the exterior surface of the container, the sealing element moves in a direction towards the interior surface of the container. Moreover, when the sealing elements contact the interior surface of the container, a seal is formed. Consequently, the fluid cannot escape from the container.

DETAILED DESCRIPTION

Exemplary embodiments of the present invention and their advantages may be understood by referring to FIGS. 1–5, like numerals being used for like corresponding parts in the various drawings.

Figure 1:
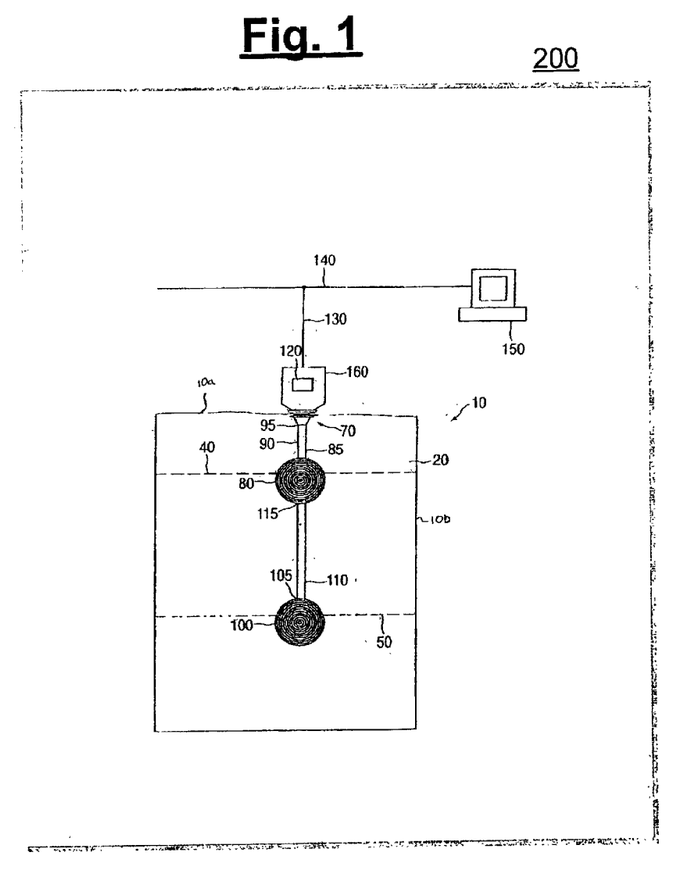
FIG. 1 is a schematic diagram of a first exemplary embodiment of a particular arrangement of an assembly according to the present invention for determining a characteristic of fluid within a container.

Referring to FIG. 1, an exemplary embodiment of a particular arrangement 200 (e.g., a sensor arrangement) for determining a characteristic of a sample fluid 20 (e.g., beer) within a container (e.g., a tank, such as a beer tank) is provided. For example, the particular arrangement 200 of the present invention may be similar to the arrangement described in U.S. Pat. No. 6,234,019. Specifically, the particular arrangement 200 may include a housing arrangement 70, a first sensor 80, a first extension 90, a second sensor 100, a second extension 110, a transmitter 120, a first data bus 130, a second data bus 140 and a computer system 150.

Figure 1A:
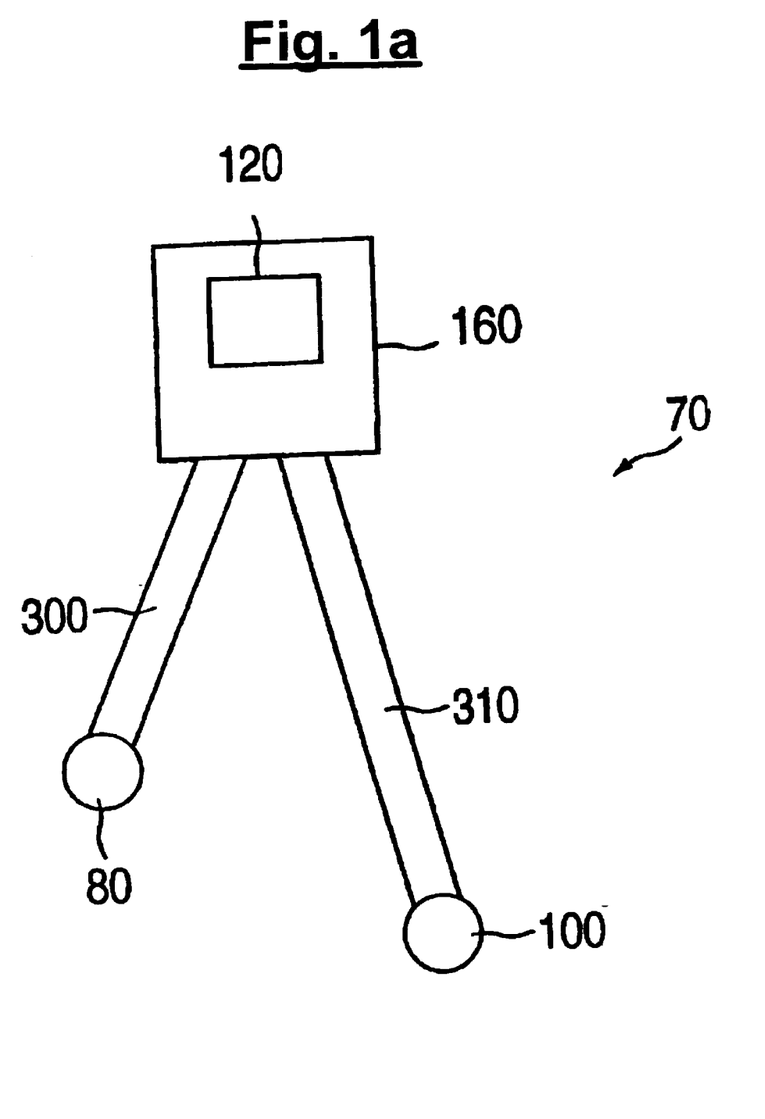
FIG. 1a is a schematic diagram of a variation of the first exemplary embodiment of the particular arrangement of FIG. 1 according to the present invention.

The housing arrangement 70 can include the first extension 90 and/or the second extension 110. The first sensor 80, the second sensor 100 and/or the transmitter 120 can be provided within the housing arrangement 70. Alternatively, the first sensor 80, the second sensor 100 and/or the transmitter 120 may be externally coupled to the housing arrangement 70. For example, the transmitter 120 can be positioned outside a container 10, and the first and second sensors 80, 100 can be positioned inside the container 10. The first extension 90 may have a first end 85 and a second end 95. Similarly, the second extension 110 can have a first end 105 and a second end 115. Moreover, the first end 105 of the second extension 110 can be coupled to the second sensor 100, and the second end 115 of the second extension 110 may be coupled to the first sensor 80. Further, the first end 85 of the first extension 90 can be coupled to the first sensor 80, and the second end 95 of the first extension 90 may be coupled to a container portion 160 of the housing arrangement 70. The transmitter 120 may be coupled to the container portion 160, or alternatively, can be positioned inside container portion 160. For example, the first extension 90 can be vertically aligned with the second extension 110, such that the first extension 90 and the second extension 100 are a single tube separated by the first sensor 80. As depicted in FIG. 1a, in a variation of the exemplary embodiment of the present invention, a first extension 300 and a second extension 310 can be changed to separate tubes extending from container portion 160.

In another exemplary embodiment of the present invention, the transmitter 120 can be coupled to the first data bus 130 (e.g., a high speed bus, such as a Fieldbus, etc.), and the first data bus 130 can be coupled to a second data bus 140 (e.g., a high speed bus, such as a Fieldbus, etc.). Moreover, the second data bus 140 can be coupled to the computer system 150, such that the transmitter 120 may be in communication with the computer system 150 via the first data bus 130 and the second data bus 140. In this exemplary embodiment of the present invention, there may be a plurality of first data buses 130 coupled to the computer system 150 via the second data bus 140, such that a plurality of transmitters 120 associated with different containers 10 may be in communication with the computer system 150. Alternatively, the second data bus 140 can be eliminated from the particular arrangement 200 and the first data bus 130 can be directly coupled to the computer system 150.

In operation, the container 10 may contain the sample fluid 20, and a sensor fluid (e.g., a static sensor fluid, such as silicon oil, fluorolube oil, silicone oil, propylene glycol oil, etc.) can be provided within tubes (not shown) which are situated within the housing arrangement 70. As such, the housing arrangement 70 maintains the sensor fluid separate from the sample fluid 20. As described in detailed in U.S. Pat. No. 6,234,019, the first sensor 80 and/or the second sensor 100 can communicate with the transmitter 120 via the sensor fluid. For example, a first portion of the sensor fluid can be provided in a first of the tubes, and a second portion of the sensor fluid can be provided in a second of the tubes. Moreover, the first sensor 80 may act on the first portion of the sensor fluid, and the second sensor 100 may act on the second portion of the sensor fluid.

Specifically, in this exemplary embodiment of the present invention, a portion of the housing arrangement 70 may be lowered into the sample fluid 20, such that the first sensor 80 is situated within the sample fluid 20 at a first fluid level 40, and the second sensor 100 is situated within the sample fluid 20 at a second fluid level 50. As described in more detail below with reference to FIG. 3, the particular arrangement 200 then can be affixed to the container 10 using a further arrangement 250 e.g. to a top portion or codes of the container 10 thereof outside of the opening through which the assembly is placed in the container 10 and an assembly 350. After the particular arrangement 200 is affixed to the container 10, the first sensor 80 may sense the fluid pressure at the first fluid level 40, and the second sensor 100 may sense the fluid pressure at the second fluid level 50. Moreover, the pressure sensed by the first sensor 80 may displace the first portion of the sensor fluid. Similarly, as described in U.S. Pat. No. 6,234,019, the pressure sensed by the second sensor 100 may displace the second portion of the sensor fluid. Further, the transmitter 120 can transmit a signal or a plurality of signals including data associated with the displacement of the sensor fluid, and the computer system 150 can calculate a density of the sample fluid based on such data.

Figure 2:
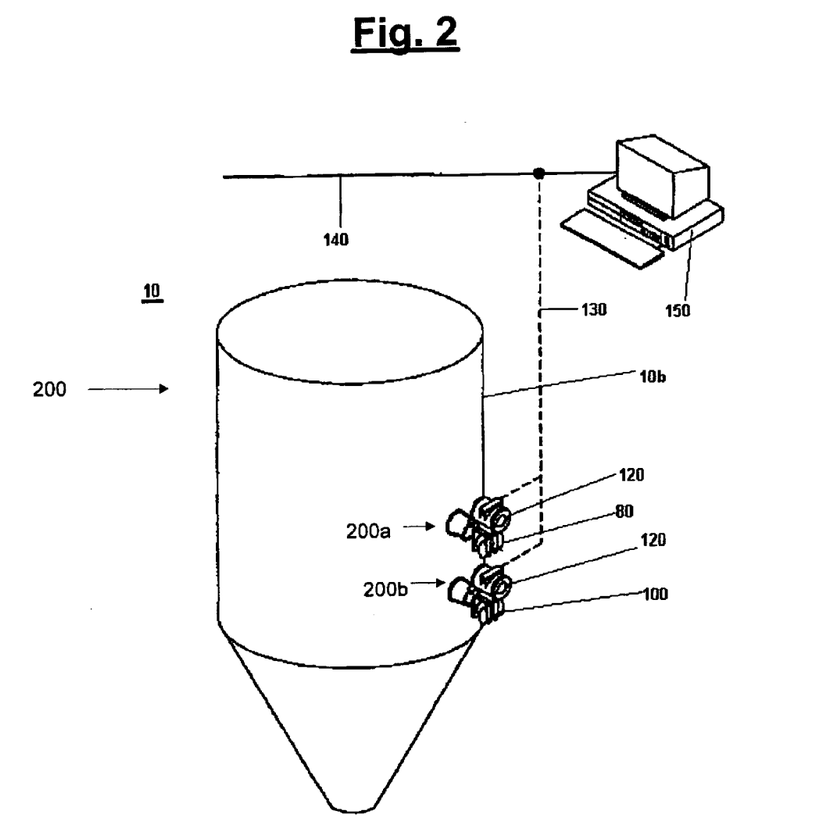
FIG. 2 is a schematic diagram of a second exemplary embodiment of the particular arrangement of the assembly according to the present invention for determining the characteristic of the fluid within the container.
Figure 3:
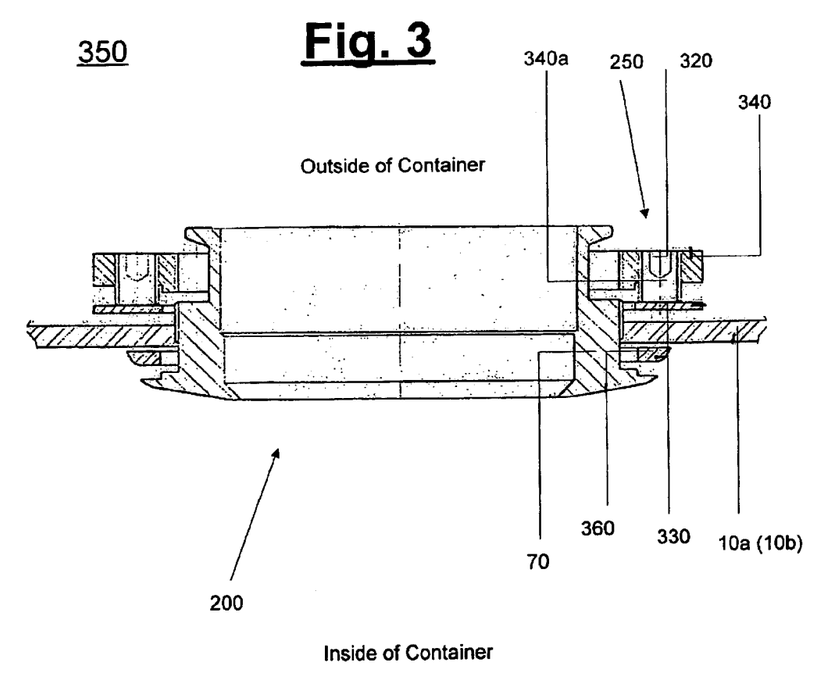
FIG. 3 is a side cross-sectional view of an exemplary embodiment of the assembly adapted to be affixed to the container according to the present invention.
Figure 4:
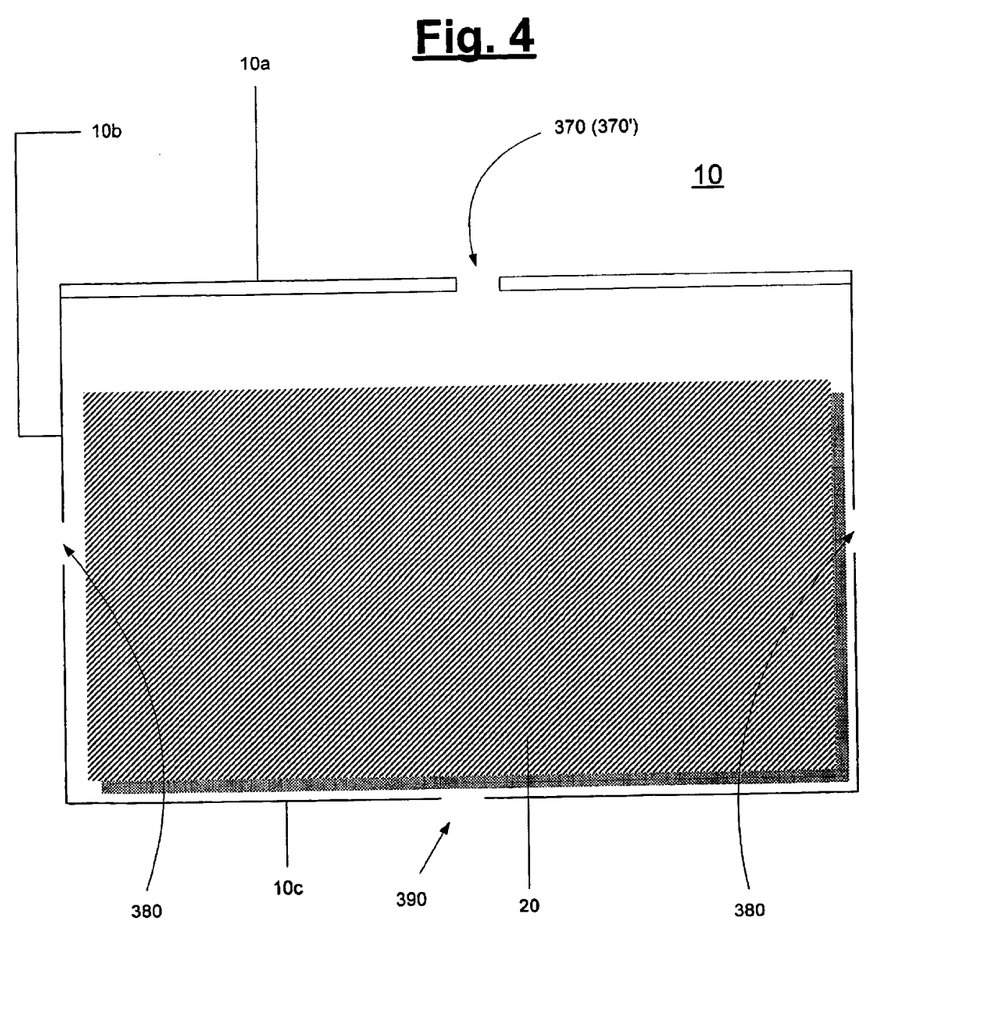
FIG. 4 is an exemplary illustration of the container having an opening formed therethrough which facilitates the assembly as shown in FIG. 1.

Referring to FIG. 2, another exemplary embodiment of the particular arrangement 200 is depicted. For example, the particular arrangement of this embodiment of the present invention may be similar to an arrangement described in U.S. Pat. No. 5,827,963 except that the particular arrangement 200 is not affixed to the container 10 using bolts, screw, etc. The features and advantages of this embodiment of the present invention as shall be described below with reference to FIG. 3 are substantially similar to the features and advantages of the above-described embodiments of the present invention, and thus are not discussed herein. In this embodiment, the particular arrangement 200 includes a first particular arrangement 200a and a second particular arrangement 200b. Each of the particular arrangements 200a and 200b are affixed to a side wall, 10b of the container 10. For example, the first particular arrangement 200a may be positioned above the second particular arrangement 200b, such that the first particular arrangement 200a can sense the fluid pressure at the first fluid level 40 and the second particular arrangement 200b can sense the fluid pressure at the second fluid level 50. Moreover, a portion of the housing arrangement 70 can be positioned within an opening 370' formed in the side wall 10b, and the first sensor 80, the second sensor 100, and the transmitter 120 can be positioned outside the container 10.

Referring to FIG. 3, a side cross-sectional view of an exemplary embodiment of the assembly 350 which is adapted to be affixed to the container 10 is provided. The assembly 350 can include the particular arrangement 200 according to any of the above-described embodiments of the present invention, and the further arrangement 250. For example, the further arrangement 250 can be adapted to affix the particular arrangement 200 of the assembly 350 to the container 10 when a portion of the particular arrangement 200 is situated within an opening 370, 380, 390 (shown in FIG. 4) in the container 10 by applying a contact pressure to a surface (e.g., an interior surface or an exterior surface) of the container 10 without piercing (e.g., without penetrating) the surface of the container 10. For example, the opening 370, 380, 390 can be formed in a top portion 10a of the container 10 which is adapted to cover the container 10, a side wall 10b of the container 10, or a bottom portion 10c of the container 10. Moreover, the further arrangement 250 can include one or more securing elements 320 (e.g., a threaded element, such as a bolt or a screw) positioned outside of the container 10. Each of the securing elements 320 may be directly or indirectly connected to the housing arrangement 70, and can also be adapted to apply the contact pressure to the surface of the container 10 without piercing such surface. For example, each securing element 320 can apply the contact pressure to the exterior surface of the container 10 when rotated in a predetermined direction.

The further arrangement 250 also can include a contact member 330 (e.g., a washer) positioned between a corresponding securing element 320 and the container 10. As such, each securing element 320 may apply the contact pressure to the surface of the container 10 via the corresponding contact member 330. The further arrangement 250 can also include a plate or flange portion 340 having one or more holes 340a formed therethrough. The plate portion 340 can be connected directly or indirectly to the housing arrangement 70, and each hole 340a may be adapted to receive a corresponding securing element 320.

The assembly 350 also can include one or more sealing elements 360. Each of the sealing elements 360 may be directly or indirectly connected to the housing arrangement 70, and can be mechanically coupled to the further arrangement 250. Moreover, when such securing element 320 applies contact pressure to a surface of the container 10, the sealing element 360 moves in a direction towards another surface which is provided opposite the contact pressure surface of the container 10. For example, when the securing element 320 applies contact pressure to the exterior surface of the container 10, the sealing element 360 moves in a direction towards the interior surface of the container 10. Specifically, when one or more sealing elements 360 contact the interior surface of the container 10, a seal is formed therebetween. Consequently, the sample fluid 20 is prevented from escaping or leaking from the container 10.

Moreover, in an exemplary embodiment of the present invention, the securing element 360 may not have any sharp edges or roughened surfaces. As such, the residue would not likely to collect on the securing element 360, so as not to affect the sample fluid 20. As described-above, in the exemplary embodiment of the present invention, after the particular arrangement 200 of the assembly 350 has been affixed to the container 10 using the further arrangement 250, the density of the sample fluid 20 can be determined by the particular arrangement 200.

Figure 5:
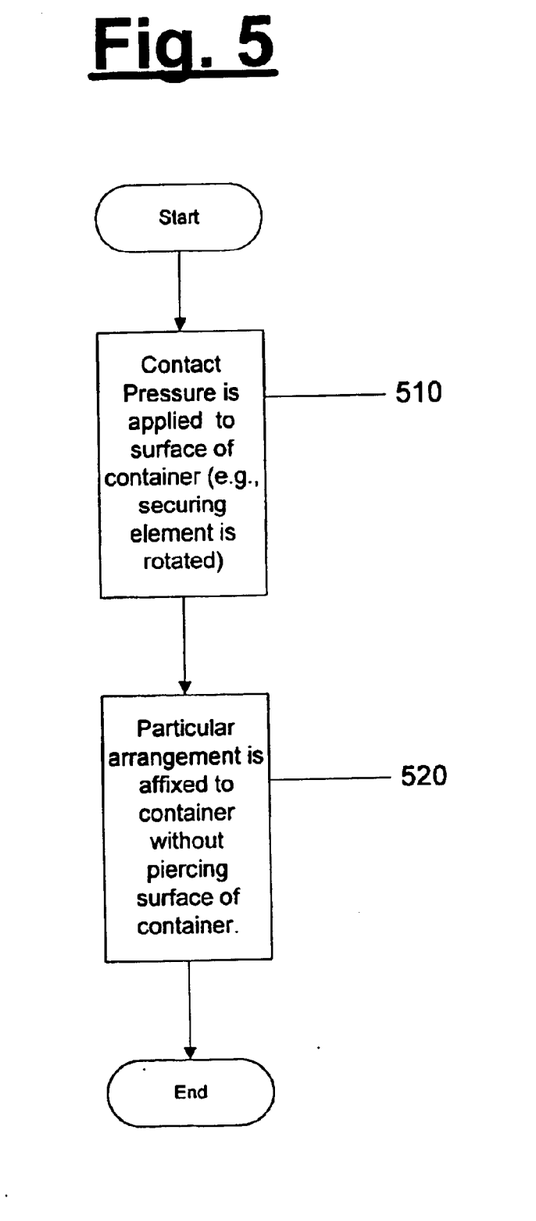
FIG. 5 is a flow diagram of an exemplary embodiment of a method according to the present invention for affixing the assembly to the container.

Referring to FIG. 5, a flow diagram of an exemplary embodiment of a method according to the present invention for affixing the assembly 350 of FIG. 3 to the container 10 is depicted. In step 510, a contact pressure is applied to a surface of the container 10. For example, the contact pressure can be applied by rotating the securing element or elements 320 in a predetermined direction. In step 520, the particular arrangement 200 is affixed to the container 10 without piercing the surface of the container 10 when at least a portion of the particular arrangement 200 is situated within an opening 370 of the container 10. For example, when the contact pressure is applied to the surface of the container 10, the sealing element or elements 350 may be drawn into contact with the container 10, thereby forming a seal with the container 10.

While the invention has been described in connecting with preferred embodiments, it will be understood by those of ordinary skill in the art that other variations and modifications of the preferred embodiments described above may be made without departing from the scope of the invention. Other embodiments will be apparent to those of ordinary skill in the art from a consideration of the specification or practice of the invention disclosed herein. It is intended that the specification and the described examples are considered as exemplary only, with the true scope and spirit of the invention indicated by the following claims.

What is claimed is:

1. An assembly adapted to be affixed to a container which contains a sample fluid, comprising:
    a first arrangement positioned in a vicinity of an opening in the container; and
    a second sensor arrangement which includes at least one portion situated within the opening, wherein the first arrangement is adapted to affix the second sensor arrangement to the container without piercing a surface of the container by applying a contact pressure to the surface of the container.

2. The assembly of claim 1, wherein the surface of the container is an exterior surface of the container.

3. The assembly of claim 2, wherein the second sensor arrangement comprising a housing arrangement which contains a first sensor fluid and a second sensor fluid, wherein the housing arrangement maintains the first sensor fluid and the second sensor fluid separate from the sample fluid, and wherein at least one portion of the housing arrangement is positioned within the container.

4. The assembly of claim 3, wherein the second arrangement further comprises a first sensor positioned one of within the container and outside the container at a first fluid level of the sample fluid, wherein the first sensor is one of coupled to the housing arrangement and positioned inside the housing arrangement, and wherein the first sensor is adapted to detect a first fluid pressure at the first fluid level by acting on the first sensor fluid.

5. The assembly of claim 4, wherein the second arrangement comprises a second sensor positioned one of within the container and outside the container at a second fluid level of the sample fluid, wherein the second sensor is at least one of coupled to the housing arrangement and positioned inside the housing arrangement, wherein the second sensor is adapted to detect a second fluid pressure at the second fluid level by acting on the second sensor fluid, and wherein the second sensor is positioned a predetermined distance from the first sensor.

6. The assembly of claim 5, wherein the second arrangement further comprises a transmitter positioned outside the container, wherein the transmitter is at least one of coupled to the housing arrangement and positioned inside the housing arrangement, and wherein the transmitter is adapted to communicate with the first sensor via the first sensor fluid and with the second sensor via the second sensor fluid.

7. The assembly of claim 6, wherein the transmitter further is adapted to generate at least one signal corresponding to the density of the sample fluid.

8. The assembly of claim 7, wherein the second arrangement further comprises a calculating device coupled to the transmitter, wherein the calculating device is adapted to calculate the density of the sample fluid based on the at least one signal.

9. The assembly of claim 3, wherein the first arrangement comprises at least one securing element positioned outside the container, wherein the at least one securing element is one of directly and indirectly connected to the housing arrangement, and wherein the at least one securing element is adapted to apply the contact pressure to the exterior surface of the container without piercing the exterior surface of the container.

10. The assembly of claim 9, further comprising at least one sealing element which is one of directly and indirectly connected to the housing arrangement, wherein, when the at least one securing element applies the contact pressure to the exterior surface of the container, the sealing element moves in a direction towards an interior surface of the container.

11. The assembly of claim 10, wherein the at least one securing element is at least one threaded element, wherein the first arrangement further comprises at least one contact member positioned between the at least one securing element and the container, and wherein the at least one threaded element is adapted to apply the contact pressure to the exterior surface of the container via the at least one contact member when rotated in a predetermined direction.

12. The assembly of claim 11, wherein the at least one threaded element is at least one of a bolt and a screw.

13. The assembly of claim 10, wherein the first arrangement further comprises a plate having at least one hole formed therethrough, wherein the plate is connected to the housing arrangement, and wherein the at least one hole is adapted to receive the at least one securing element.

14. The assembly of claim 3, wherein the first arrangement comprises a plurality of securing elements positioned outside of the container, wherein each of the securing elements is one of directly and indirectly connected to the housing arrangement, and wherein each of the securing elements is adapted to apply the contact pressure to the exterior surface of the container without piercing the exterior surface of the container.

15. The assembly of claim 14, wherein the first arrangement further comprises a plate having a plurality of holes formed therethrough, wherein the plate is connected to the housing arrangement, and each of the holes are adapted to receive one of the securing elements.

16. The assembly of claim 15, wherein the holes formed in the plate are positioned about 180 degrees apart from each other.

17. The assembly of claim 1, wherein the opening is formed in one of a top portion covering the container and a side wall of the container.

18. The assembly of claim 1, wherein the container is a tank.

19. The assembly of claim 1, wherein the contact pressure is applied to a particular portion of the surface of the container without piercing the particular portion.

20. The assembly of claim 10, wherein the at least one sealing element and the container form a seal therebetween.

21. A method of affixing an assembly to a container which contains a sample fluid, comprising the steps of:
    providing the assembly in or at an opening of the container; and
    affixing a particular sensor arrangement to the container without piercing a surface of the container by applying a contact pressure by the assembly to the surface of the container in a vicinity of the opening, wherein at least one portion of the particular sensor arrangement is situated within the opening of the container.

22. The method of claim 21, wherein the surface of the container is an exterior surface of the container.

23. The method of claim 22, wherein the particular sensor arrangement comprising a housing arrangement which contains a first sensor fluid and a second sensor fluid, wherein the housing arrangement maintains the first sensor fluid and the second sensor fluid separate from the sample fluid, and wherein at least one portion of the housing arrangement is positioned within the container.

24. The method of claim 23, wherein the particular arrangement comprises a first sensor positioned one of within the container and outside the container at a first fluid level of the sample fluid, wherein the first sensor is at least one of coupled to the housing arrangement and positioned inside the housing arrangement, and wherein the first sensor is adapted to detect a first fluid pressure at the first fluid level by acting on the first sensor fluid.

25. The method of claim 24, wherein the particular arrangement further comprises a second sensor positioned one of within the container and outside the container at a second fluid level of the sample fluid, wherein the second sensor is at least one of coupled to the housing arrangement and positioned inside the housing arrangement, wherein the second sensor is adapted to detect a second fluid pressure at the second fluid level by acting on the second sensor fluid, and wherein the second sensor is positioned a predetermined distance from the first sensor.

26. The method of claim 25, wherein the particular arrangement further comprises a transmitter positioned outside the container, wherein the transmitter is at least one of coupled to the housing arrangement and positioned inside the housing arrangement, and wherein the transmitter is adapted to communicate with the first sensor via the first sensor fluid and with the second sensor via the second sensor fluid.

27. The method of claim 26, wherein the transmitter further is adapted to generate at least one signal corresponding to the density of the sample fluid.

28. The method of claim 27, wherein the particular arrangement further comprises a calculating device coupled to the transmitter, wherein the calculating device is adapted to calculate the density of the sample fluid based on the at least one signal.

29. The method of claim 23, the step of affixing the particular arrangement to the container comprising the sub-step of applying the contact pressure to the exterior surface of the container using a further arrangement, the further arrangement comprising at least one securing element which is positioned outside the container, wherein the at least one securing element is one of directly and indirectly connected to the housing arrangement, and wherein the at least one securing element is adapted to apply the contact pressure to the exterior surface of the container without piercing the exterior surface of the container.

30. The method of claim 29, further comprising at least one sealing element which is one of directly and indirectly connected to the housing arrangement, wherein the step of applying the contact pressure to the exterior surface of the container comprises the sub step of moving the at least one sealing element in a direction towards an interior surface of the container.

31. The method of claim 30, wherein the at least one securing element is at least one threaded element, wherein the further arrangement further comprises at least one contact member positioned between the at least one securing element and the container, and wherein the step of applying the contact pressure to the exterior surface of the container further comprises the sub step of rotating the at least one threaded element in a predetermined direction, such that the at least one threaded element applies the contact pressure via the at least one contact member.

32. The method of claim 31, wherein the at least one threaded element is at least one of a bolt and a screw.

33. The method of claim 29, wherein the further arrangement further comprises a plate having at least one hole formed therethrough, wherein the plate is connected to the housing arrangement, and wherein the at least one hole is adapted to receive the at least one securing element.

34. The method of claim 21, wherein the opening is formed in one of a top portion covering the container and a side wall of the container.

35. The method of claim 21, wherein the container is a tank.

36. The assembly of claim 21, wherein the contact pressure is applied to a particular portion of the surface of the container without piercing the particular portion.

37. The method of claim 30, wherein the sub step of moving the at least one sealing element in the direction towards the container comprises the step of forming a seal between the at least one sealing element and the container.

38. An assembly adapted to be affixed to a container which contains a sample fluid, comprising:

a first arrangement positioned in a vicinity of an opening in the container; and a second arrangement which includes at least one portion situated within the opening, wherein the first arrangement is adapted to affix the second arrangement to the container without piercing an internal surface of the container by applying a contact pressure to the internal surface of the container.

39. A method of affixing an assembly to a container which contains a sample fluid, comprising the steps of:

providing the assembly in or at an opening of the container; and affixing a particular arrangement to the container without piercing an internal surface of the container by applying a contact pressure by the assembly to the internal surface of the container in a vicinity of the opening, wherein at least one portion of the particular arrangement is situated within the opening of the container.

* * * * *